(12) United States Patent
Cataldo et al.

(10) Patent No.: US 9,034,846 B2
(45) Date of Patent: May 19, 2015

(54) USE OF CYCLODEXTRIN FOR TREATMENT AND PREVENTION OF BRONCHIAL INFLAMMATORY DISEASES

(71) Applicant: UNIVERSITE DE LIEGE, Angleur (BE)

(72) Inventors: Didier Cataldo, Olne (BE); Brigitte Evrard, Embourg (BE); Agnes Noel, Durbuy (BE); Jean-Michel Foldart, Trooz (BE)

(73) Assignee: UNIVERSITE DE LIEGE, Angleur (BE)

( * ) Notice: Subject to any disclaimer, the term of this patent is extended or adjusted under 35 U.S.C. 154(b) by 48 days.

(21) Appl. No.: 13/804,626

(22) Filed: Mar. 14, 2013

(65) Prior Publication Data

US 2013/0196947 A1 Aug. 1, 2013

Related U.S. Application Data

(63) Continuation-in-part of application No. 13/478,743, filed on May 23, 2012, now abandoned, which is a continuation of application No. 12/846,241, filed on Jul. 29, 2010, now abandoned, which is a continuation of application No. 11/664,999, filed as application No. PCT/EP2005/054966 on Sep. 30, 2005, now Pat. No. 7,829,550.

(30) Foreign Application Priority Data

Oct. 10, 2004 (EP) .................................... 04104957

(51) Int. Cl.
*A61K 31/724* (2006.01)
*A61P 11/00* (2006.01)
*A61K 9/00* (2006.01)

(52) U.S. Cl.
CPC ............ *A61K 31/724* (2013.01); *Y10S 514/826* (2013.01); *A61K 9/0078* (2013.01)

(58) Field of Classification Search
None
See application file for complete search history.

(56) References Cited

U.S. PATENT DOCUMENTS

| 4,020,160 A | * | 4/1977 | Bernstein et al. | ............... 514/58 |
| 4,054,736 A | | 10/1977 | Hayashi | |
| 5,840,713 A | | 11/1998 | Weisz | |
| 2006/0128611 A1 | * | 6/2006 | Lewis et al. | ....... 514/8 |

OTHER PUBLICATIONS

Vozone, C. et al "Complexation of budesonide in cyclodextrins . . . " J. Incl. Phen. Macrocyc. Chem. (2002) vol. 44, pp. 111-115.*
Sin, D. et al "Contemporary management of chronic obstructive pulmonary disease" JAMA (2003) vol. 290, No. 17, 2301-2312.*
Szente, L. et al "Highly soluble cyclodextrin derivatives . . . " Adv. Drug Deliv. Rev. (1999) vol. 36, pp. 17-28.
Shiotani, K. et al "Differential effects of sulfate and sulfobutyl ether . . . " Pharm. Res. (1995) vol. 12, No. 1, pp. 78-84.
Greene, C. et al "TLR-induced inflammation in cystic fibrosis . . . " J. Immunol. (2005) vol. 174, pp. 1638-1646.
Salerno, F. et al "Airway inflammation in patients . . . " Respir. Med. (2004) vol. 98, pp. 25-28.
Ghambarian, M. et al "COPD: can prevention be improved?" Preventive Med. (2004) vol. 39, pp. 337-343.
Van Schayck, O. et al "is there any role for allergen avoidance . . . " J. Allergy Clin. Immunol. (2007) vol. 119, pp. 1323-1328.
Scichilone, N. et al "Clinical implications of airway hyperresponsiveness . . . " Int. J. COPD (2006) vol. 1, No. 1, pp. 49-60.
Global Initiative for Chronic Obstructive Lung Disease (2009) pp. 1-90.
Doherty, D. "The pathophysiology of airway dysfunction" Am. J. Med. (2004) vol. 117, No. 12A, pp. 11S-23S.
Hansen, E. et al "Bronchodilator reversibility in COPD . . . " Eur. Resp. J. (2005) vol. 26, pp. 6-7.
Patent Abstracts of Japan, vol. 12, No. 186, May 31, 1988 & JP62292719A (Kaken Pharmaceut Co Ltd), Dec. 19, 1987, 1 pg.
Patent Abstracts of Japan, vol. 11, No. 349, Nov. 14, 1987 & JP62123132A (Michio Nakanishi), Jun. 4, 1987, 1 pg.
Rajewski et al, Jour. of Pharmaceutical Sci., vol. 85, No. 11, Nov. 1996, pp. 1142-1169, Pharmaceutical Applications of . . .

* cited by examiner

*Primary Examiner* — Leigh Maier
(74) *Attorney, Agent, or Firm* — Jacobson Holman, PLLC

(57) ABSTRACT

The invention provides the use of a cyclodextrin compound for the manufacturing of a medicament for the treatment or prevention of bronchial inflammatory diseases, particularly for asthma and chronic obstructive pulmonary disease (COPD).

3 Claims, 10 Drawing Sheets

USE OF CYCLODEXTRIN FOR TREATMENT AND PREVENTION OF BRONCHIAL INFLAMMATORY DISEASES

CROSS-REFERENCES TO RELATED APPLICATIONS

This is a continuation-in-part application of application Ser. No. 13/478,743, filed May 23, 2012, which is a continuation application of application Ser. No. 12/846,241, filed Jul. 29, 2010, which in turn is a continuation application of application Ser. No. 11/664,999, filed Apr. 10, 2007 (now U.S. Pat. No. 7,829,550), which in turn is a national stage application of PCT/EP2005/054966, filed Sep. 30, 2005 and published in English, claiming the priority benefit of European Application No. 04104957.8, filed Oct. 10, 2004.

FIELD OF THE INVENTION

The present invention relates to the use of cyclodextrin compound for the treatment and prevention of bronchial inflammatory diseases, including chronic obstructive pulmonary disease (COPD).

BACKGROUND OF THE INVENTION

Compounds for the treatment and prevention of bronchial inflammatory diseases including COPD are classified in the art as bronchodilator also called reliever medications or non-bronchodilators antinflammatory agents referred to as controller agents, on the basis of their pharmacodynamic effects.

Short-acting bronchodilators such as inhaled beta agonist or anticholinergics are considered reliever medications. Corticosteroids, cromolyn sodium, nedocromil sodium, sustained-release theophylline and long-acting beta agonist are considered controller medications, since they are used to achieve and maintain control of symptoms and are used daily on a long-term basis.

Among reliever medication, inhaled 132-adrenergic agonists are drugs for relief of symptoms due to acute airway obstruction. They have a rapid onset of action and a 3-6 h duration of activity. Unfortunately they have side effects such as tachycardia, palpitations and tremor that often disapear during chronic administration.

Anticholinergic agents induce airway smooth muscle relaxation. Their activity is not as effective as beta agonists in asthma but is more prolonged (6 to 8 hours).

Among controller medications, glucocorticosteroids are effective agents with anti-inflammatory effects. Unfortunately, their side effects include adrenal suppression, osteoporosis, growth suppression, weight gain, hypertension, diabetes, dermal thinning, cataracts, myopathy and psychotic actions. These effects are dose related and are usually seen with systemic administration. Local side effects, including oral candidiasis and dysphonia may occur at lower doses of inhaled glucocorticoids.

Cromolyn sodium and nedocromil sodium are also classified as controller agents, because of their similar clinical profile. They inhibit bronchoconstriction induced by neurally mediated events.

Theophylline is generally considered as a bronchodilator but has weak bronchodilator activity in therapeutic doses. It may also have anti-inflammatory properties. The dose-related adverse effects of theophylline are nausea, nervousness, anxiety and tachycardia.

Lipoxygenase inhibitors and leukotriene receptor agonists are also controller agents. They alter the pathological effects of leukotrienes derived from the 5-lipoxygenation of arachidonic acid. They can inhibit the bronchospastic effects of allergens, exercice, cold dry air, and aspirin allergy. Both are efficaceous in alleviating symtoms and improving pulmonary function during 4-6 weeks of therapy in patients with moderate asthma.

There is therefore a need for improved compounds which can be used for the treatment or prevention of bronchial inflammatory diseases including COPD.

BRIEF SUMMARY OF THE INVENTION

It is now surprisingly found that cyclodextrin is useful as active component for the treatment or prevention of bronchial inflammatory diseases, including COPD.

The invention therefore provides the use of cyclodextrin compound for the treatment or prevention of bronchial inflammatory disease including COPD in a host mammal in need of such treatment.

By cyclodextrin compound, one means cyclodextrin as well as their pharmaceutically acceptables salts, enantiomeric forms, diastereoisomers and racemates.

By cyclodextrin, one means cyclic oligosaccharides produced by enzymatic degradation of starch such as described in "Cyclodextrin Technology, J Szejtli, Kluwer Academic Publishers 1998, pp 1-78", and which are composed of a variable number of glucopyrannose units (n), mostly 6, 7 or 8. These cyclodextrins are respectively named $\alpha$, $\beta$ and $\gamma$ cyclodextrins ($\alpha$ CD, $\beta$ CD, $\gamma$CD).

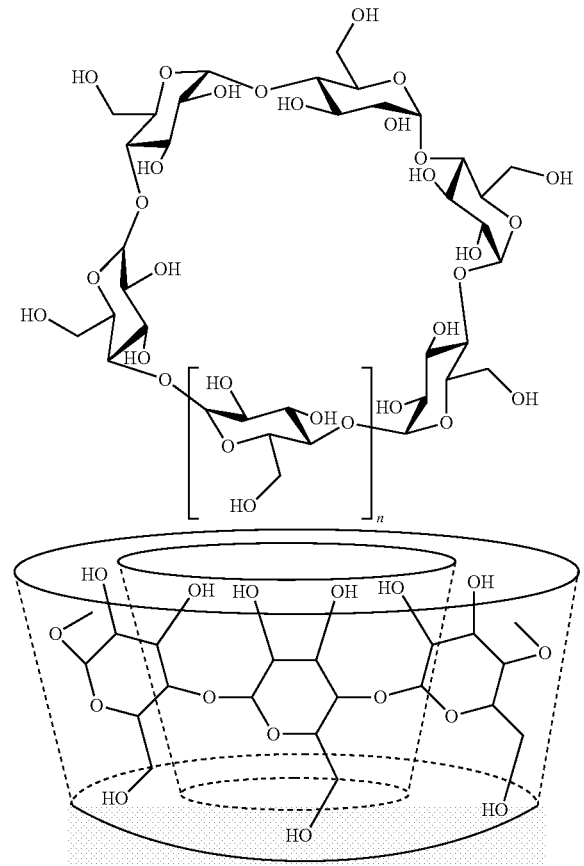

n = 6 $\alpha$-cyclodextrin n = 7 $\beta$-cyclodextrin n = 8 $\gamma$-cyclodextrin Cyclodextrin is also represented by CD hereafter.

Cyclodextrin compound according to the invention is cyclodextrin per se, alkyl-cyclodextrin (R-CD) wherein R is methyl, ethyl, propyl and butyl; carboxyalkyl-cyclodextrin (CR-CD), etherified-cyclodextrin (RO-CD), sulfoalkyl-cyclodextrin (SR-CD), hydroxyalkyl-cyclodextrin (HR-CD), glucosyl-cyclodextrin, di and triglycerides-cyclodextrin or a combination thereof and their pharmaceutically acceptable salts which are at least water soluble in an amount of 0.5 gr/100 ml at 25° C.

The water-soluble cyclodextrin compound preferably used in the present invention refers to a cyclodextrin compound having water solubility of at least that of β-cyclodextrin (1.85 g/100 ml). Examples of such water-soluble cyclodextrin compound are sulfobutylcyclodextrin, hydroxypropylcyclodextrin, maltosylcyclodextrin, and salts thereof. In particular, sulfobutyl-β-cyclodextrin, hydroxypropyl-β-cyclodextrin, maltosyl-β-cyclodextrin, and salts thereof.

Other preferred cyclodextrin compound according to the invention are methylcyclodextrins (products of the cyclodextrins methylation) such as 2-O-methylβ-cyclodextrin; dimethylcyclodextrin (DIMEB) (preferably substituted in 2 and in 6); trimethylcyclodextrin (preferably substituted in 2, 3 and 6);

"random methylated" cyclodextrins (RAMEB or RM) (preferably substituted at random in 2, 3 and 6, but with a number of 1,7 to 1,9 methyl by unit glucopyrannose), hydroxypropylcyclodextrins (HPCD), hydroxypropylated cyclodextrins preferably substituted randomly mainly in position 2 and 3 (HP-βCD, HP-γ CD)), sulfobutylethercyclodextrins (SB-ECD), hydroxyethyl-cyclodextrins, carboxymethylethylcyclodextrins, ethylcyclodextrins, cyclodextrins amphiphiles obtained by grafting hydrocarbonated chains in the hydroxyl groups and being able to form nanoparticles, cholesterol cyclodextrins and triglycerides-cyclodextrins obtained by grafting cyclodextrins monoaminated (with a spacer arm) as described in Critical Review in Therapeutic drug Carrier Systems, Stephen D. Bruck Ed, Cyclodextrin-Enabling Excipient; their present and future use in Pharmaceuticals, D. Thomson, Volume 14, Issue 1 p 1-114 (1997)

Most preferred cyclodextrins compounds are
β-cyclodextrin with optionally a chemical function grafted on the glucopyrannose units such as hydroxypropyl-βcyclodextrin (HPβCD), sulfonylbutylether-βcyclodextrin (SBEβCD), random methylated-βcyclodextrin (RMβCD), dimethyl-βcyclodextrin (DIMEβCD), trimethyl-βcyclodextrin (TRIMEβCD), hydroxybutyl pcyclodextrin (HBβCD), glucosyl βcyclodextrin, maltosyl βcyclodextrin and 2-O-methyl βcyclodextrin (Crysmeb), or a combination thereof and their pharmaceutically acceptable salts.

The cyclodextrin compounds according to the invention are produced by the well-known enzymatic degradation of starch such as the method described in "Cyclodextrin Technology, J Szejtli, Kluwer Academic Publishers 1998, pp 1-78, followed by grafting of an appropriate chemical group.

The invention further provides the use of such cyclodextrin compound for the manufacturing of a medicament for the treatment or prevention of bronchial inflammatory diseases to a patient in need of such treatment.

According to the invention the cyclodextrin compound has to be administered to the patient over several months or years (especially in case of prevention). The cyclodextrin compound is administered preferably as aerosol, with non-toxic doses ranging between nanomolar and molar concentrations.

The present invention relates to a method used for treating bronchial inflammatory diseases, preferably asthma and chronic obstructive pulmonary disease (COPD) in a host mammal in need of such treatment, e.g., a patient suffering from such a disease, by the application of a cyclodextrin compound according to the invention in a pharmaceutically effective amount. The present invention provides cyclodextrins for controlling inflammation in COPD and COPD-related diseases.

In COPD patients, there is a significant neutrophilic inflammation in the bronchial walls leading to progressive destruction of airways structures by the repeated productions of proteases and oxidants (oxygen reactive species). To date, marketed therapies are not able to adequately decrease or prevent this neutrophilic inflammation in COPD patients. In particular, it is well know that inhaled or oral steroids display no efficiency against neutrophilic inflammation. For example, a study of S. Culpitt et al (Am J Respir Crit. Care Med (1999) 160: 1635-1639) performed in COPD patients reports the lack of efficacy of high doses inhaled steroids in COPD-related neutrophilic inflammation and chemotactic agents for neutrophils (mainly IL-8 in humans).

It is well established that neutrophils are the major inflammatory cells in COPD and that these cells are attracted in the airways by potent chemotactic agents such as IL-8 in human (V. Murugan et al, Exp Lung Res. 2009 August; 35(6):439-85). In rodents, the cytokine system is similar but chemotactic agents responsible for neutrophils chemotaxis are slightly different and include CXCL-1 (also named KC) as a major chemoattractant playing a similar role to human IL-8 especially documented in the context of tobacco smoke exposure (V. Lagente Clin Exp Pharmacol Physiol. 2008 May; 35(5-6):601-5). Lipopolysaccharide (LPS), a component of external membrane of gram-negative bacteria, is able to induce a neutrophilic inflammation with characteristics similar to that observed in COPD and is therefore considered as a suitable model of COPD. Pathways activated by LPS that lead to neutrophilic inflammation are similar to those observed in COPD and include CXCL-1 production (A. Roos Biochem Biophys Res Commun. 2012 Jun. 22; 423(1):134-9).

Asthma is an inflammatory disease of the bronchial tree related or not to an allergen exposure. This inflammation provokes symptoms in patients by stimulating the bronchial smooth muscles to contract, enhancing the mucus secretion, and inducing bronchial morphological changes thought to be an aggravating factor regarding the course of the disease. Airway hyperresponsiveness is a hallmark of the disease and is responsible for most of symptoms. Bronchial tree is a very complex tissue with many cell types (as for example epithelial cells, smooth muscle cells, inflammatory cells, nerves, mucus producing cells, fibroblasts) and the bronchial remodelling events which comprise many aspects mainly consist in a deposition of extracellular matrix components in the bronchial walls, a smooth muscle hyperplasia and a hyperplasia of the mucus producing cells. The use of cyclodextrin compounds according to the invention inhibits the inflammatory cells influx in the compartments of bronchoalveolar lavage and peribronchial tissue and inhibits the hyperresponsiveness defined as an abnormal response to stimulating agents such as methacholine. The disease and current treatments are reviewed in, e.g., GINA Workshop Report, Global Strategy for Asthma Management and Prevention (NIH Publication No. 02-3659) and Fabbri, L. M., and Hurd, S. S., Eur. Respir. J. 22 (2003) 1-2.

The invention therefore further relates to a method for treating bronchial inflammatory diseases in a patient suffering from such a disease, using a cyclodextrin compound according to the invention in a therapeutically effective amount.

The invention preferably further relates to a method for treating emphysema in a patient suffering from such a disease, using cyclodextrin compounds according to the invention. In such a disease, the alveolar walls are destroyed by proteolytic processes and this destruction impairs the transfer of oxygen to the blood. In such a disease, physiological problems also occurs because of the derived hyperinflation which causes abnormalities in the ventilation by causing a dysfunction of respiratory muscles and because of a hypertension in pulmonary arteries leading to cardiac failure in advanced stages.

The invention preferably further relates to a method for treating chronic obstructive pulmonary disease (COPD) in a patient suffering from such a disease, using cyclodextrin compounds according to the invention. In such a disease, the bronchial walls of small airways are remodelled by proteolytic processes and this remodelling and fibrosis induce an airway obstruction which can be measured by spirometry. In such a disease, physiological problems also occurs because of the derived hyperinflation which causes abnormalities in the ventilation/perfusion ratio and causes hypoventilation and eventually $CO_2$ accumulation.

According to the invention the cyclodextrin compound has to be administered over several months or years, to the patient in need of such a therapy. The cyclodextrin compounds are administered preferably by the aerosolization of a liquid or powder composition, with non-toxic doses ranging between micro and molar concentrations per kg and day.

A further preferred object of the invention is a pharmaceutical composition of cyclodextrin compound according to the invention for the treatment of bronchial inflammatory diseases, and its use, containing a cyclodextrin or a salt thereof and preferably a water-soluble cyclodextrin derivative (water soluble being defined as a solubility of at least 0.5 g/100 ml water at 25° C.).

The pharmaceutical compositions are aqueous compositions having physiological compatibility. The compositions include, in addition to cyclodextrin or a salt thereof, auxiliary substances, buffers, preservatives, solvents and/or viscosity modulating agents. Appropriate buffer systems are based on sodium phosphate, sodium acetate or sodium borate. Preservatives are required to prevent microbial contamination of the pharmaceutical composition during use. Suitable preservatives are, for example, benzalkonium chloride, chlorobutanol, methylparabene, propylparabene, phenylethyl alcohol, sorbic acid. Such preservatives are used typically in an amount of 0.01 to 1% weight/volume.

The cyclodextrin compound of the present invention exhibits its effects through either oral administration, parenteral administration or topical administration, and it is preferably formed into a composition for parenteral administration, particularly an injection composition or topical administration, particularly an aerosol composition. Such aerosol composition is for example a solution, a suspension, a micronised powder mixture and the like. The composition is administered by using a nebulizer, a metered dose inhaler or a dry powder inhaler or any device designed for such an administration.

Examples of galenic compositions include tablets, capsules, powders, granules and the like. These may be produced through well known technique and with use of typical additives such as excipients, lubricants, and binders.

Suitable auxiliary substances and pharmaceutical compositions are described in Remington's Pharmaceutical Sciences, 16th ed., 1980, Mack Publishing Co., edited by Oslo et al. Typically, an appropriate amount of a pharmaceutically-acceptable salt is used in the composition to render the composition isotonic. Examples of pharmaceutically acceptable substances include saline, Ringer's solution and dextrose solution. pH of the solution is preferably from about 5 to about 8, and more preferably from about 7 to about 7.5.

A preferred pharmaceutical composition for nebulization comprises cyclodextrin (CD), NaCl and water. The solution is prepared by dissolving CD in 100 ml of purified water, adding NaCl by stirring so as to dissolve them and complete with water so as to obtain 200 ml of solution. Preferably the solution is sterilized by filtration through a 0.22 μm polypropylene membrane or by a steam sterilization process.

Especially preferred composition is a combination of (for 200 ml of solution):

10-50 g CD, preferably 20 g CD, preferably HPβCD; sodium chloride 1.2-1.5 g, preferably 1.42 g (isotonicity) and water, preferably pyrogen-free, sterile, purified water ad 200 ml.

Such a composition is useful for the treatment of bronchial inflammatory diseases.

Most preferred composition is a combination of 2-O-methylβCD with sodium chloride 1.2-1.5 g, preferably 1.42 g (isotonicity) and water, preferably pyrogen-free, sterile, purified water ad 200 ml.

In summary, the present invention provides a method for the treatment of COPD (Chronic obstruction pulmonary disease) in a host mammal in need of such treatment, comprising the step of administering an effective amount of cyclodextrin compound to the mammal, wherein the cyclodextrin compound is selected from the group consisting of b-cyclodextrin, hydroxypropyl-bcyclodextrin, sulfolbutylether-bcyclodextrin, random methylated-bcyclodextrin, dimethylbcyclodextrin, trimethyl-bcyclodextrin, hydroxypropyl b-cyclodextrin, hydroxybutyl bcyclodextrin, glucosyl-bcyclodextrin, maltosyl-bcyclodextrin, 2-O-methyl-bcyclodextrin or a combination thereof and their pharmaceutically acceptable salts. Preferbaly, the cyclodextrin compound is hydroxypropyle-beta-cyclodextrine and its pharmaceutically acceptable salts. Preferably, the mode of administration is inhalation.

The following examples, references, and figures are provided to aid the understanding of the present invention. It is understood that modifications can be made in the procedures set forth without departing from the invention.

DETAILED DESCRIPTIONS OF THE INVENTION

Example 1

Figure 1:
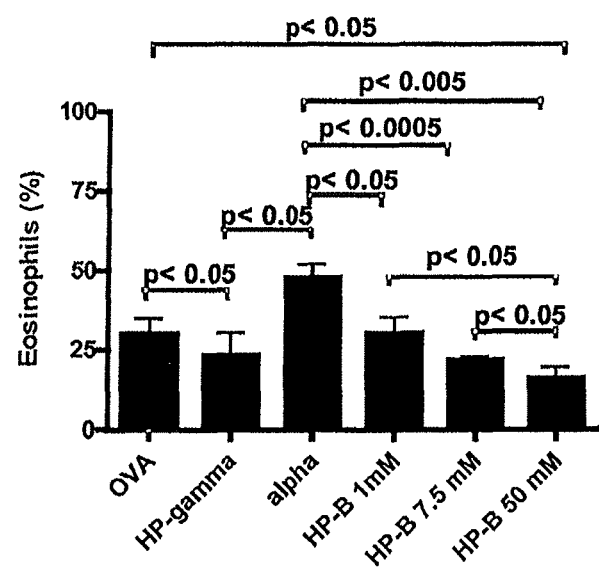
FIGS. 1-2 Effects of inhalation of cyclodextrin compound on BAL eosinophil percentage (FIG. 1) and peribronchial inflammation score (FIG. 2). Controls are mice exposed to ova by inhalation and placebo by inhalation (OVA)

Use of Compositions Containing HP-β-Cyclodextrin for Therapy of Allergen-Induced Airway Inflammation and Bronchial Hyperresponsiveness in a Mouse Model of Asthma Materials HP-β-CD (degree of substitution=0.64) was obtained from Roquette (France).

α- and HP-γ-CD were obtained from Wacker Chemie Gmbh (Germany). Apyrogenic phosphate buffered saline (PBS) was purchased from Bio-Wittaker (Verviers, Belgium). Methacholine was from Sigma-Aldrich (Germany).

All other materials were of analytical grade. Sterile water for injection was used throughout this study. Sterile, apyrogenic and isotonic CD solutions were prepared at 1, 7.5 and 50 mM for HP-β-CD and α-CD and at 50 mM for HP-γ-CD. Cyclodextrins were tested following the Bacterial Endotoxin Test described in USP XXVI using *Limulus Amebocyte* Lysate (LAL). Osmolalities of all the solutions were measured by a Knauer Automatic semi-micro Osmometer and adjusted to the value of 300 mOsm/kg by the addition of an adequate amount of NaCl. A terminal sterilization of the solutions was performed by steam sterilization process.

Methods

Aerosol was produced by using an ultrasonic nebuliser SYSTAM, the vibration frequency of which is 2.4 MHz with variable vibration intensity and ventilation levels. Vibration intensity was fixed in position 6 and the ventilation level was 25 (t½) l/min.

Characterization of Nebulized Aerosol

Aerosol size distribution emitted from CDs solutions was determined with a laser size analyzer Mastersizer (Malvern, Orsay, France). Ten milliliters of each solution were directly nebulized in the laser beam. The mouth piece was held at 1 cm from the center of the laser beam. The resulting aerosol was aspirated on the opposite side of the beam. Environmental temperature and relative humidity were maintained constant, that is to say at 20° C. and 40-45%. Triplicates of each measurement were performed and compared to controls of PBS. The results are expressed as the percentage of droplets comprised in the range 0.5 to 5.79 μm and the median diameter. The concentration of droplets in the air evaluated by the obscuration percentage of the laser beam was in the same range for each experiment (15-25%). A comparison of the MMAD, the GSD and the percentage of droplets comprised in the range of 0.5 to 5.79 μm of all the CDs solutions with the corresponding values for PBS demonstrated that the presence of CDs in the solution did not influence the droplet size distribution in the aerosols. A fraction of droplets comprised in the range of 0.5 to 5.79 μm close to 65% was obtained in each experiment.

Sensitisation, Allergen Exposure and Therapeutic Protocols.

In order to study modulation of airway inflammation, males BALB/c mice of 6 to 8 weeks old were sensitized by intraperitoneal injection of 10 μg ovalbumin (OVA) (Sigma Aldrich, Schnelldorf, Germany) emulsified in aluminum hydroxyde (AlumInject; Perbio, Erembodegem, Belgium) on days 1 and 8. Mice were subsequently exposed to allergens by daily inhalation of an aerosol of OVA 1%, for 30 minutes, generated by ultrasonic nebulizer (Devilbiss 2000), from day 21 to 27. Mice were subjected to inhalation of β-CD, HP-β-CD HP 1, 7.5, 50 mM and HP-β-CD 50 mM 30 minutes before OVA inhalation. Mice were sacrificed performed on day 28 as previously reported by Cataldo and al in Am. J. Pathol 2002; 161(2):491-498.

Bronchoalveolar Lavage Fluid (BAL)

Immediately after assessment of airway responsiveness, and 24 hours after the last allergen exposure.

Mices were sacrificed and a bronchoalveolar lavage was performed using 4×1 ml PBS-EDTA 0.05 mM (Calbiochem, Darmstadt, Germany) as previously described by Cataldo D D, Tournoy K G, Vermaelen K et al. in Am J Pathol 2002; 161(2):491-498. Cells were recovered by gentle manual aspiration. After centrifugation of bronchoalveolar fluid (BALF) (1200 rpm for 10 minutes, at 4° C.), the supernatant was frozen at −80° C. for protein assessment and the cell pellet was resuspended in 1 ml PBS-EDTA 0.05 mM. The differential cell counts were performed on cytocentrifuged preparations (Cytospin) after staining with Diff-Quick (Dade, Belgium).

Pulmonary Histology and Tissue Processing

After BAL, the thorax was opened and the left main bronchus was clamped. The left lung was excised and frozen immediately at −80° C. for protein and mRNA extraction. The right lung was infused with 4 ml paraformaldehyde 4%, embedded in paraffin and used for histology. Sections of 5 μm thickness were cut off from paraffin and were stained with haematoxylin-eosin. The extent of peribronchial inflammation was estimated by a score calculated by quantification of peribronchial inflammatory cells, as previously described by Cataldo D D, Tournoy K G, Vermaelen K et al. in Am J Pathol 2002; 161(2):491-498. A value of 0 was adjudged when no inflammation was detectable, a value of 1 when there was occasionally inflammatory cells, a value of 2 when most bronchi were surrounded by a thin layer (1 to 5 cells) of inflammatory cells and a value of 3 when most bronchi were surrounded by a thick layer (>5 cells) of inflammatory cells. Since 5-7 randomly selected tissue sections per mouse were scored, inflammation scores are expressed as a mean value and can be compared between groups. After Congo Red staining, the eosinophilic infiltration in the airway walls was quantified by manual count and reported to the perimeter of epithelial basement membrane defining an eosinophilic inflammatory score.

The left lung was crushed using a Mikro-Dismembrator (Braun Biotech International, Gmbh Melsungen, Germany). For proteins extraction, the crushed lung tissue was incubated overnight at 4° C. in a solution containing 2M urea, 1M NaCl and 50 mM Tris (pH 7.5) and subsequently centrifuged 15 minutes at 16.000×g. The supernatant was stored at −80° C.

Bronchial Responsiveness Measurement

Twenty-four hours after the last allergen exposure, the bronchial hyper responsiveness was determined by measuring the Penh (Enhanced Pause) using a barometric plethysmograph (Emka technologies, Paris) as proposed by Hamelmann, E., et al., Am. J. Respir. Crit. Care Med. 156 (1997) 766-775). The Penh was measured at baseline and 5 mM after the inhalation of increasing doses (25, 50, 75 and 100 mM) of methacholine (Mch).

Measurements of Cytokines by ELISA

Eotaxin and IL-13 levels were assessed using commercial ELISAs (R&D systems, Abingdon, UK). Eotaxin was measured by incubation in a wheel coated with a primary antibody specifically dedicated to the recognition of the protein and after rinsing, a second antibody against eotaxin, coupled with horse radish peroxydase was used to quantify the amounts of eotaxin in the solution Measurement of Allergen Specific Serum IgE At the end of the experiment, blood was drawn from the heart for measurement of OVA specific serum IgE. Microtiter plates were coated with OVA. Serum was added followed by a biotinylated polyclonal rabbit anti-mouse IgE (S. Florquin, ULB, Brussels, Belgium). A serum pool from OVA-sensitized animals was used as internal laboratory standard; 1 unit was arbitrarily defined as 1/100 dilution of this pool.

Measurement of Eotaxin and IL-13 in Bal and Lung Protein Extracts.

IL-13 was measured by incubation in a wheel coated with a primary antibody specifically dedicated to the recognition of the protein and after rinsing, a second antibody against IL-13, coupled with horse radish peroxydase was used to quantify the amounts of eotaxin in the solution.

Statistical Analysis

Results of BAL cell count, pulmonary histology, cytokines and mRNA levels were expressed as mean+/−SEM and the comparison between the groups was performed using Mann-Whitney test. Mann-Whitney test was performed using GRAPHPAD INSTAT version 3.00 for WINDOWS 95 (GRAPHPAD SOFTWARE, San Diego, Calif., USA, WWW.GRAPHPAD.Com.). P values <0.05 were considered as significant.

Pharmacological Results:

Inflammatory Cells in the BAL.

After allergen exposure, eosinophil counts were significantly decreased after the inhalation of HP-β-CD and HP-β-CD at the dose of 50 mM. There was a dose dependent decrease in BAL eosinophils with the HP-β-CD 1, 7.5 and 50 mM inhalation. Other inflammatory cells were not present in different amounts in the BAL after HP-β-CD inhalation when compared to placebo. On the contrary, β-CD inhalation led to a tendency to increase the number of eosinophils in BAL after allergen exposure (FIG. 1).

Peribronchial Inflammation

Figure 2:
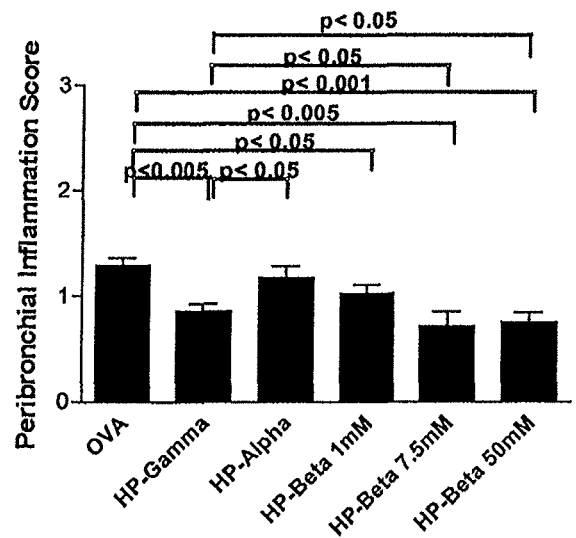

After allergen exposure, mice treated with placebo displayed a significant increase in peribronchial inflammation as quantified by the peribronchial inflammation score. Mice treated with HP-β-CD 1, 7.5, and 50 mM and HP-β-CD 50 mM were shown to have decreased inflammation score when compared to placebo treated mice. β-CD inhalation did not reduce the peribronchial inflammation score (FIG. 2).

Peribronchial Eosinophil Infiltration

Figure 3:
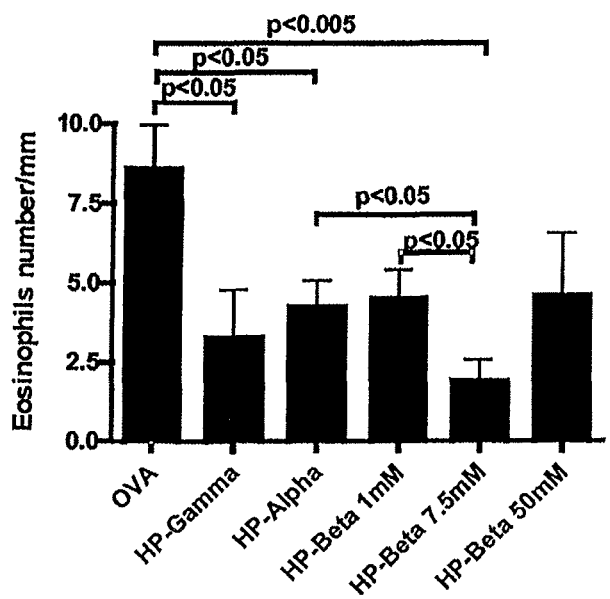
FIG. 3 Effects of inhalation of cyclodextrin compound on peribronchial eosinophils reported here as a number/mm of epithelial basement membrane.

As demonstrated previously, the allergen exposure did induce a significant increase in the number of eosinophils detectable in the peribronchial area. All CD tested induced a decrease of this infiltration and this decrease reached statistical significance for β-CD, HP-β-CD 1, 7.5, and HP-β-CD 50 mM (FIG. 3).

Bronchial Responsiveness

Figure 4:
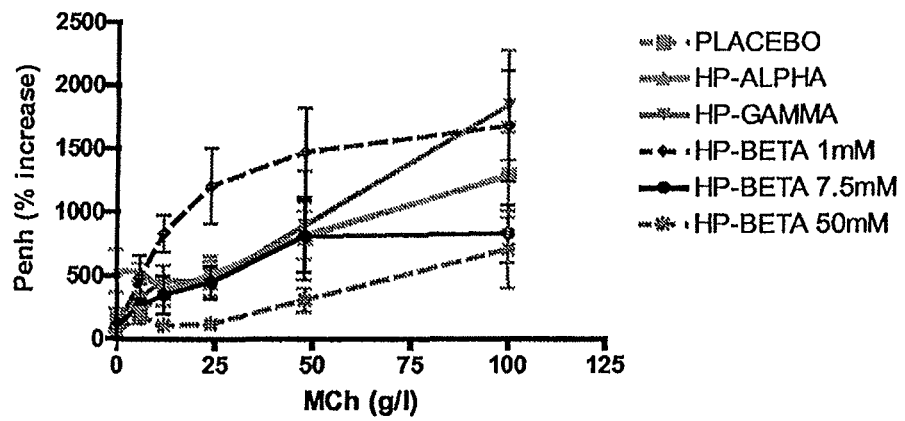
FIG. 4 Airway responsiveness measurements: Enhanced Pause (Penh) was measured in OVA exposed mice during 5 minutes after a 2 minutes inhalation of cyclodextrin or Placebo (OVA) and increasing doses of methacholine (Mch).
Figure 5:
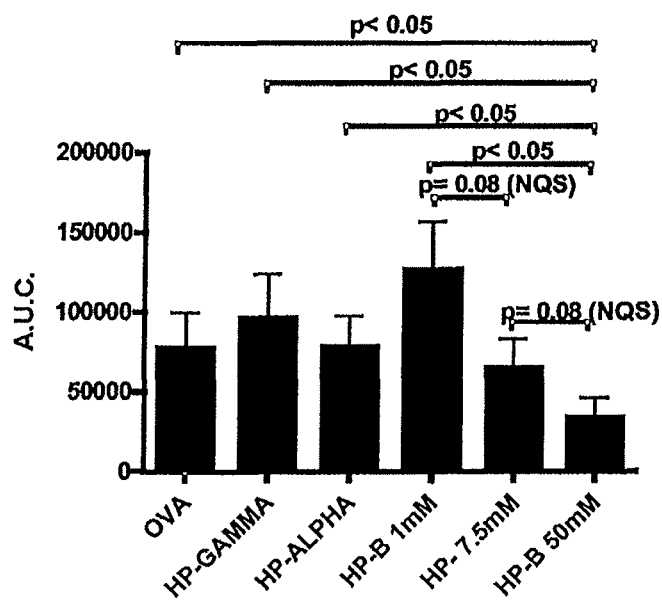
FIG. 5 Measurement of cytokines by Elisa. Eotaxin was measured by incubation in a wheel coated with a primary antibody specifically dedicated to the recognition of the protein and after rinsing, a second antibody against eotaxin, coupled with horse radish peroxydase was used to quantify the amounts of eotaxin in the solution.

The inhalation of HP-β-CD 50 mM reduced the methacholine-induced Penh increase (FIG. 4). When measuring the area under the methacholine dose-response curve (A.U.C) for different CDs, HP-β-CD 50 mM was the only to show a significant decrease (FIG. 5).

Cytokine Measurements in BAL and Lung Protein Extracts

Figure 7A:
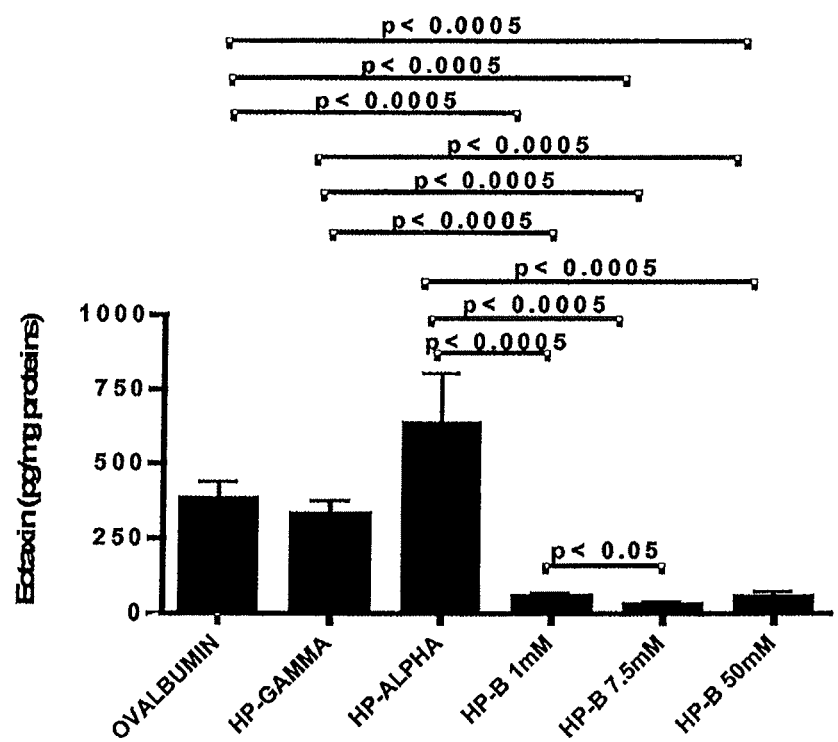
FIG. 7 Measurement of eotaxin and IL-13 in B al and lung protein extracts. IL-13 was measured by incubation in a wheel coated with a primary antibody specifically dedicated to the recognition of the protein and after rinsing, a second antibody against IL-13, coupled with horse radish peroxydase was used to quantify the amounts of eotaxin in the solution.
Figure 7B:
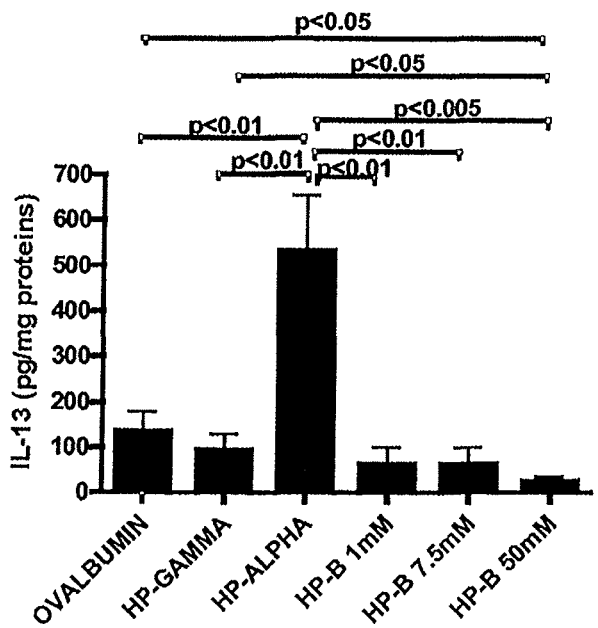
Figure 8:
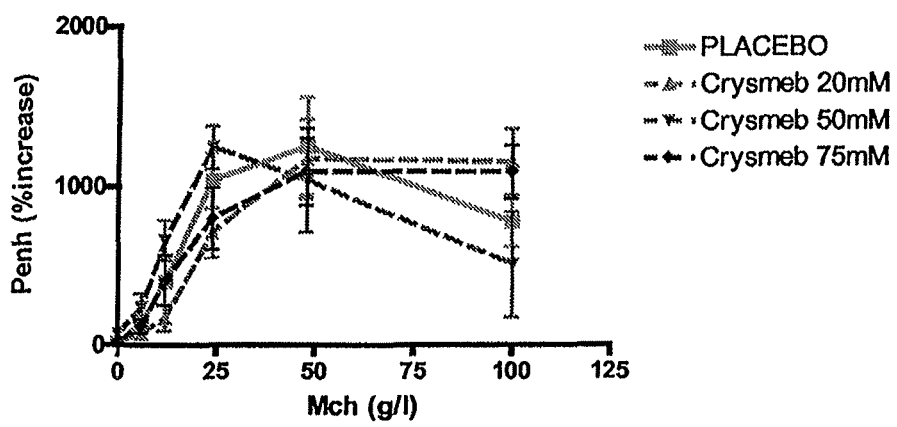
FIG. 8 Airway responsiveness measurements: Enhanced Ponse (Penh) was measured in mouses after receiving crysmeb or placebo treatment FIG. 9 Peribronchial inflammation score measured in histology when treated with various Crysmeb concentration compared to placebo (FIG. 9A) and to other cyclodextrin and fluticasone (FIG. 9B)

When compared to placebo exposed mice, all doses of HP-β-CD tested induced a decrease in levels of eotaxin measured by ELISA in lung protein extracts (FIG. 7a). IL-13 levels were decreased in BAL after HP-β-CD exposure and, on the contrary, were increased after β-CD exposure (FIG. 7b).

Measurements of Allergen-Specific IgE in Serum

Figure 6:
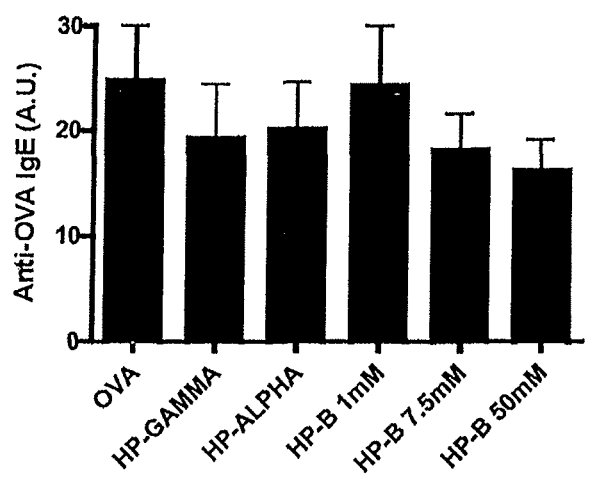
FIG. 6 Measurement of allergen specific IgE levels in serum.

There were no significant differences between the groups for the allergen sensitization as assessed by the similar levels of OVA specific IgE measured by ELISA in serum (FIG. 6).

Example 2

Use of Compositions Comprising 2-O-methyl-cyclodextrin for Therapy of Allergen-Induced Airway Inflammation and Bronchial Hyperresponsiveness in a Mouse Model of Asthma Materials Materials are identical to example 1 with the exception of the cyclodextrin compound which is here 2-O-methyl-cyclodextrin, KLEPTOSE CRYSMEB®, a product commercialised by Roquette. It has, on average, 4 methyl groups per native cyclodextrin molecule and is characterized by an average molecular weight of 1135 and a average molar degree of substitution of 0.57.

Sterile, apyrogenic and isotonic CD solutions were prepared with 10, 20, 50 and 75 mM for 2-O-methyl-cyclodextrin. Cyclodextrins were tested following the Bacterial Endotoxin Test described in USP XXVI using *Limulus Amebocyte Lysate* (LAL). Osmolalities of all the solutions were measured by a Knauer Automatic semi-micro Osmometer and adjusted to the value of 280-300 mOsm/kg by the addition of an adequate amount of NaCl. A terminal sterilization of the solutions was performed by steam sterilization process.

Methods

Same methods are used as in example 1 but in the present example we did expose mice to aerosolized CRYSMEB (10, 20, 50, 100 or 200 mM) in a standard exposure box (20×30× 15 cm) for 30 min/day during 7 days.

Pharmacological Results:

Inflammatory Cells in the BAL.

The cellular composition of the bronchoalveolar lavage was not significantly altered by the exposure to CRYSMEB. In particular, there were no differences regarding eosinophil and neutrophil counts (see table 1).

Bronchoalveolar lavage eosinophilia was significantly decreased in the groups treated by CRYSMEB. The decrease in lavage eosinophilia was comparable with that obtained with different concentrations of HP-beta-cyclodextrins or fluticasone, a commonly used inhalation steroid used as a reference therapy (table 2)

Peribronchial Inflammation

Figure 9A:
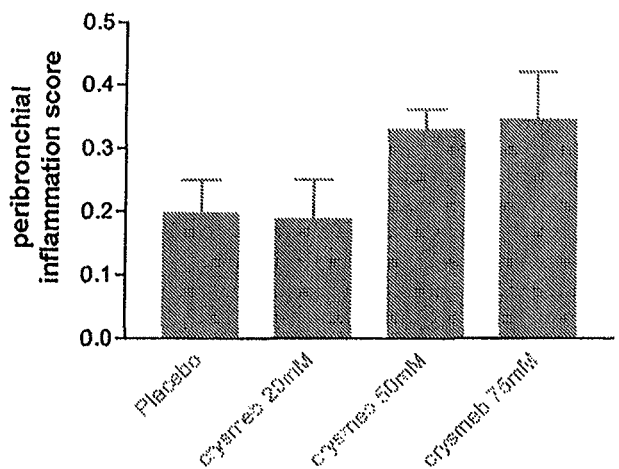
Figure 9B:
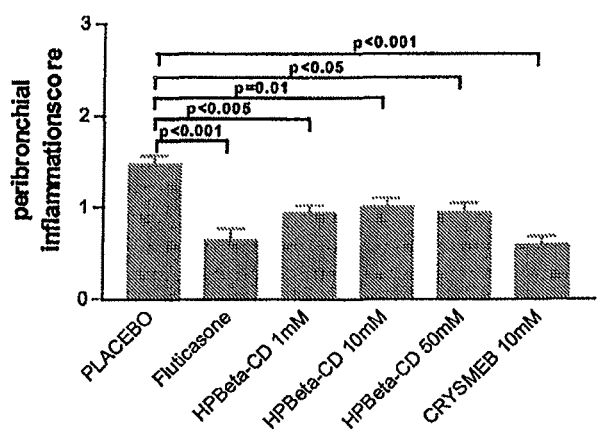

After allergen exposure, mice treated with placebo displayed a significant increase in peribronchial inflammation as quantified by the peribronchial inflammation score. Mice treated with CRYSMEB 20 mM were shown to have decreased inflammation score when compared to placebo treated mice (FIG. 9A). Peribronchial inflammation score was measured and was significantly decreased in every treatment group as compared to placebo (FIG. 9B)

Bronchial Responsiveness

Figure 10:
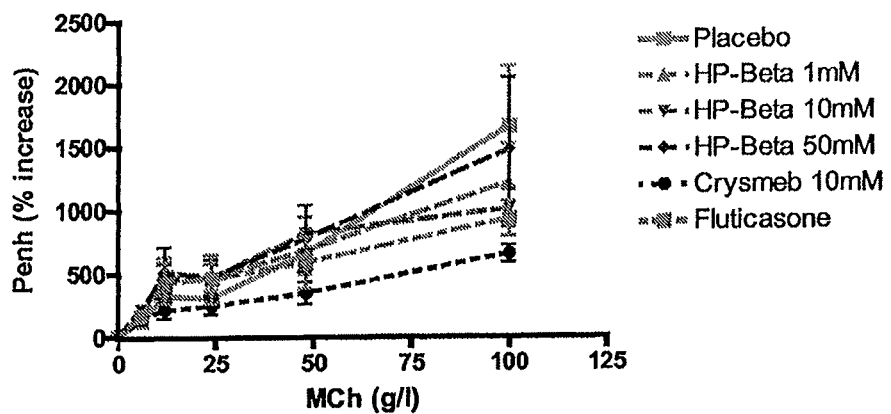
FIG. 10 Airway responsiveness measurements: comparison of cyclodextrin compounds with placebo and Fluticasone. Measurements of methacholine-induced airway response in mice exposed 7 days to allergens and receiving an inhaled therapy 30 mM before the allergen exposition.

The inhalation of CRYSMEB 10 mM reduced the methacholine-induced Penh increase (FIG. 10).

The responsiveness to methacholine was increased after allergen exposure and placebo and was significantly reduced by the treatment with CRYSMEB in an extent comparable to that obtained with fluticasone therapy (FIG. 10)

Cytokine Measurements in BAL and Lung Protein Extracts

Figure 11:
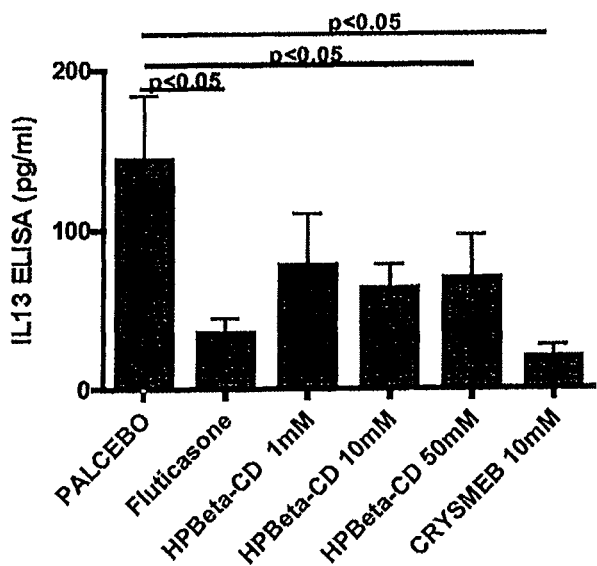
FIG. 11 Levels of IL-13 measured by Elisa in lung protein extracts.

In order to unveil mechanisms implicated in the pharmacological effect of CRYSMEB, we measured IL-13, a major Th2 cytokine implicated in the airway hyperresponsiveness and inflammation. We found that levels of IL-13 measured by ELISA in whole lung protein extracts were significantly decreased by the exposure to CRYSMEB as well as fluticasone and HP-beta-CD 50 mM. (see FIG. 11)

Example 3

Pharmaceutical Composition to be Administered in an Aerosol to a Patient in Need of Treatment for Bronchial Inflammatory Disease HP betaCD 75 mM Solution osmolality is 308 mOs/kg. pH is 7.2.

The concentration of CD compound can be modified in function of the requirements. It is preferred to adjust the tonicity by addition of NaCl.

A preferred composition for nebulization is:

For 200 ml of solution:

| | |
|---|---|
| HPβCD exempt from pyrogenic | 20.15 g (75 mM) |
| Sodium chloride | 1.42 g (isotonicity) |
| Pyrogen-free, sterile, purified water, | q.s. ad 200 ml | a) Weigh 20.15 g of HPβCD exempt from pyrogenic (3.2% $H_2O$, from ROQUETTE) and dissolve them in 100 ml of purified water.

b) Weigh 1.42 g of sodium chloride and add them to solution (a) by energetically stirring so as to dissolve them.

c) Complete with water so as to obtain 200 ml of solution.

Sterilize by filtration through a 0.22 μm polypropylene membrane.

TABLE 1 differential cell counts in the bronchoalveolar lavage measured after the exposure to different concentrations of inhaled CRYSMEB.

| | PLACEBO | Crysmeb 20 mM | Crysmeb 50 mM | Crysmeb75 mM |
|---|---|---|---|---|
| Epithelial cells (%) | 15.9714 ± 5.154 | 29.9 ± 5.909 | 36.1375 ± 4.52 | 30.8875 ± 1.349 |
| Eosinophils (%) | 0.0428 ± 0.0428 | 0.0375 ± 0.0375 | 0.1125 ± 0.0789 | 0.0375 ± 0.0375 |
| Neutrophils (%) | 0.1285 ± 0.236 | 0.0375 ± 0.1061 | 0.2 ± 0.3505 | 0.0375 ± 0.1061 |
| Lymphocytes (%) | 0.1857 ± 0.1421 | 0.425 ± 0.1485 | 0.275 ± 0.1161 | 0.075 ± 0.0491 |
| Macrophages (%) | 83.5857 ± 1.179° | 69.5 ± 5.956 | 63.1625 ± 4.695 | 68.9 ± 1.334 |

TABLE 2 differential cell counts in the bronchoalveolar lavage measured after the exposure to different concentrations of inhaled CRYSMEB.

| | PLACEBO | Fluticasone | HPBeta-CD 1 mM | HPBeta-CD 10 mM | HPBeta-CD 50 mM | CRYSMEB 10 mM |
|---|---|---|---|---|---|---|
| Epithelial cells (%) | 3.86 ± 2.551 | 22.85 ± 5.343 | 25.08 ± 3.413 | 34.44 ± 3.723 | 45.04 ± 5.534 | 36.83 ± 5.644 |
| Eosinophils (%) | 53.08 ± 4.683 | 32.92 ± 7.306* | 34.2 ± 7.705* | 27.24 ± 4.98* | 12.18 ± 4.366* | 8.84 ± 2.946* |
| Neutrophils (%) | 3.03 ± 1.333 | 1.85 ± 1.093 | 0.36 ± 0.1563 | 0.83 ± 0.5838 | 0.72 ± 0.3992 | 1.26 ± 0.4587 |
| Lymphocytes (%) | 3.62 ± 1.576 | 1.68 ± 0.7115 | 0.48 ± 0.1869 | 0.21 ± 0.08571 | 0.12 ± 0.12 | 0.214 ± 0.1079 |
| Macrophages (%) | 36.25 ± 5.016 | 40.52 ± 3.122 | 39.75 ± 5.427 | 37.114 ± 3.878 | 41.86 ± 9.043 | 52.714 ± 6.49 |
| Total cells ($10^4$/ml) | 220.42 ± 81.709 | 75.92 ± 11.922 | 74.92 ± 14.396 | 114.43 ± 33.245 | 37.33 ± 10.683 | 131.93 ± 33.637 |

Example 4

Used Inhaled hydroxypropyl-β-cyclodextrin to Address Allergen- or LPS-Induced Inflammation in Rodents Experimental Protocol:

In ovalbumin (OVA)-induced inflammation model, mice were immunized by intraperitoneal injection of OVA (10 μg) (Sigma Aldrich, Schnelldorf, Germany) and aluminium hydroxyde on days 0 and 7. From days 21 to 25, mice were exposed to inhalation of 1% OVA or PBS (phosphate buffer saline) for 30 minutes. Airway hyperresponsiveness was measured on day 26 before sacrifice. Mice were either exposed to aerosolized hydroxypropyl-beta-cyclodextrin (15 mM) or PBS for 30 mM 6 hours before allergen exposure.

After sacrifice, thorax was opened and the right lungs were excised and snap frozen in liquid nitrogen for protein extraction. The left lung was insufflated at constant pressure with 4% paraformaldehyde and embedded in paraffin for further histological analysis. A peribronchial inflammation score was applied on each hematoxylin-eosin stained slide as previously reported (Cataldo et al Am J Pathol 2002). A value from 0 to 2 was adjudged to each bronchus. Score of 0 corresponded to bronchi without inflammation; score 1 to occasional mononuclear cells observed around bronchi, and score 2 to 1 to 5 layer(s) of inflammatory cells around bronchi. Six bronchi per mice were counted and statistical analysis was performed by using GraphPad Program. Lung tissues were crushed and total protein extracts were prepared by incubating crushed lung tissues in a 2M urea solution. Tissue lysates were centrifuged for 15 mM at 16100×g. ELISA for CXCL-1 on lung protein extracts were assessed using antibodies from R&D Systems and the R&D Duoset® Elisa Development kit (R&D Systems, Minneapolis, Minn., USA).

Figure 12:
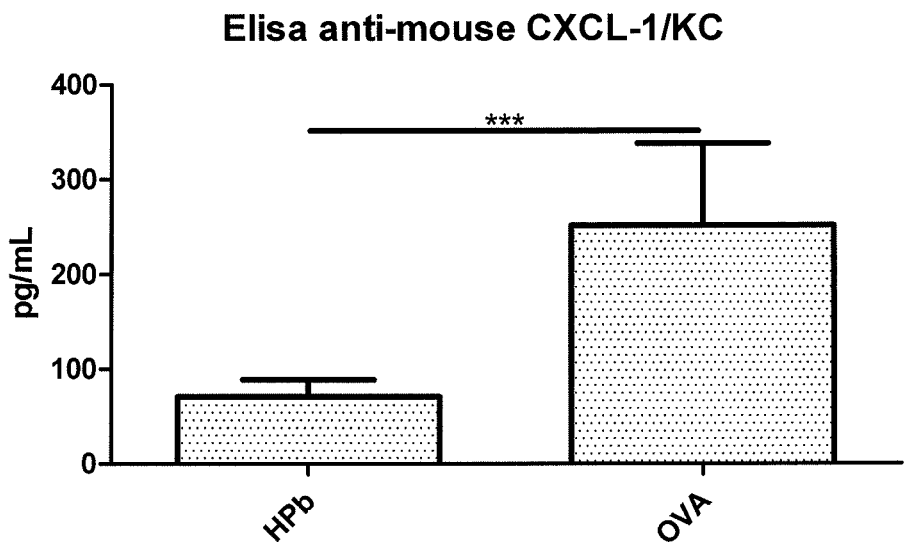
FIG. 12 Measurement of CXCL-1 by ELISA in whole lung tissue extracts (crushed in liquid nitrogen) $p<0.01$ (n=8/group).

Results:

We already reported that overall inflammation was lower as well as bronchial responsiveness to methacholine. As allergens are able to generate neutrophilic inflammation by activation of chemotactic factors, we addressed the potential efficacy of these compounds to decrease levels of neutrophil chemoattractants in mouse lungs after allergen exposure. Levels of CXCL-1, a major neutrophil chemoattractant were significantly decreased in lung protein extracts of cyclodextrins-treated mice (HPb in FIG. 12) as compared to placebo-exposed mice (OVA in FIG. 12). In summary, there is a decreased production of chemotactic agents for neutrophils after exposure to cyclodextrins in an allergen-induced inflammation model in mice.

Example 5

Used Inhaled Hydroxypropyl-β-Cyclodextrin to Address Allergen- or LPS-Induced Inflammation in Rodents Experimental Protocol:

In lipopolysaccharide (LPS)-induced inflammation model, mice were exposed to 3 μg LPS diluted in 100 μl of PBS or PBS (phosphate buffer saline) only administered by direct tracheal instillations at day 1 and 5 of the protocol. Mice were daily exposed either to aerosolized hydroxypropyl-beta-cyclodextrin (15 mM) or PBS for 30 min from day 0 to 5 (6 hours after LPS or sham exposure at days 1 and 5). Mice were sacrificed at day 6.

After sacrifice, thorax was opened and the right lungs were excised and snap frozen in liquid nitrogen for protein extraction. The left lung was insufflated at constant pressure with 4% paraformaldehyde and embedded in paraffin for further histological analysis. A peribronchial inflammation score was applied on each hematoxylin-eosin stained slide as previously reported (Cataldo et al Am J Pathol 2002). A value from 0 to 2 was adjudged to each bronchus. Score of 0 corresponded to bronchi without inflammation; score 1 to occasional mononuclear cells observed around bronchi, and score 2 to 1 to 5 layer(s) of inflammatory cells around bronchi. Six bronchi per mice were counted and statistical analysis was performed by using GraphPad Program. Lung tissues were crushed and total protein extracts were prepared by incubating crushed lung tissues in a 2M urea solution. Tissue lysates were centrifuged for 15 min at 16100×g. ELISA for CXCL-1 on lung protein extracts were assessed using antibodies from R&D Systems and the R&D Duoset® Elisa Development kit (R&D Systems, Minneapolis, Minn., USA).

Figure 13:
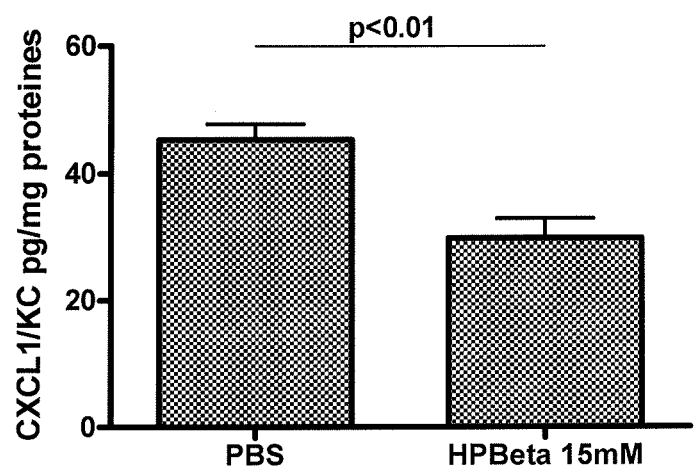
FIG. 13 Measurements of CXCL-1 levels in lung protein extracts of mice exposed to aerosolized placebo (PBS) or hydroxypropyl-β-cyclodextrin (HPBeta) at 15 mM (n=6/group).
Figure 14:
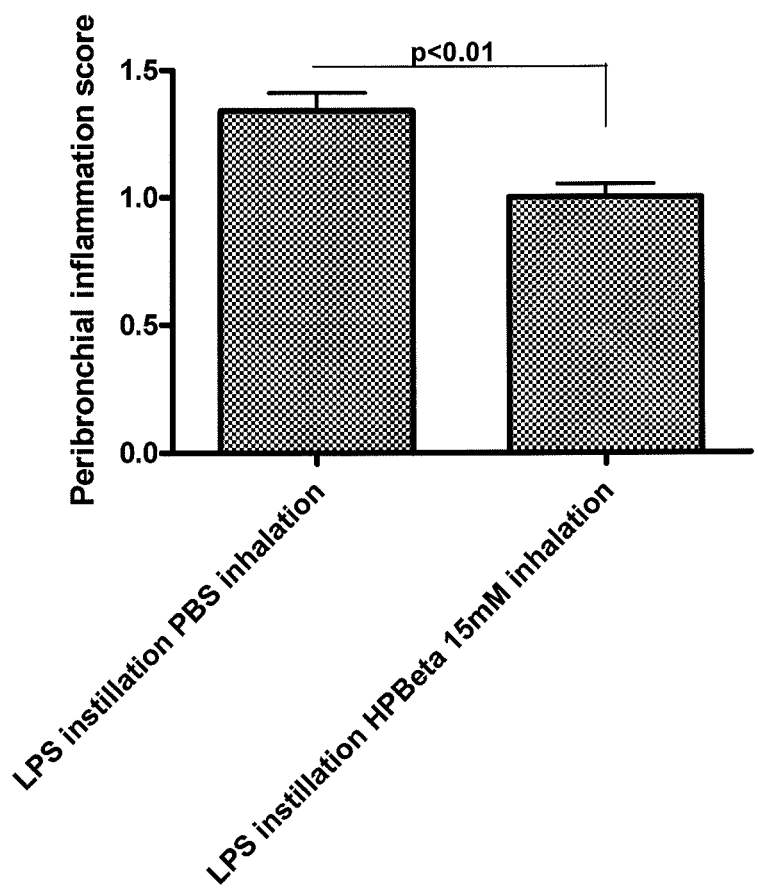
FIG. 14 Measurements of peribronchial inflammation by histology (see <<experimental protocol>> section for description of the scoring system) (n=6/group).

Results:

Levels of CXCL-1 (a chemotactic agent for neutrophils) were significantly decreased after treatment of animals inhaled with hydroxypropyl-β-cyclodextrin as compared to placebo-treated mice (FIG. 13). Peribronchial inflammation was significantly lower in the hydroxypropyl-β-cyclodextrin-treated group as compared to placebo-exposed animals (FIG. 14).

CONCLUSION

Overall, these data demonstrate that hydroxypropyl-β-cyclodextrin is able to decrease the production of CXCL-1, a potent chemotactic agent for neutrophils in various inflammatory conditions and LPS-induced peribronchial inflammation suggesting a usefulness of this compound for treatment of COPD.

The invention claimed is:

1. A method for the treatment of COPD (Chronic obstruction pulmonary disease) in a host mammal in need of such treatment, comprising the step of administering a composition consisting essentially of an effective amount of cyclodextrin compound to the mammal, wherein the cyclodextrin compound is selected from the group consisting of b-cyclodextrin, hydroxypropyl-bcyclodextrin, sulfolbutylether-bcyclodextrin, random methylated-bcyclodextrin, dimethyl-bcyclodextrin, trimethyl-bcyclodextrin, hydroxypropyl b-cyclodextrin, hydroxybutyl bcyclodextrin, glucosyl-bcyclodextrin, maltosyl-bcyclodextrin, 2-O-methyl-bcyclodextrin or a combination thereof and their pharmaceutically acceptable salts.

2. The method for the treatment of COPD according to claim 1 wherein the cyclodextrin compound is hydroxypropyle-beta-cyclodextrine and its pharmaceutically acceptable salts.

3. The method according to claim 1 wherein the mode of administration is inhalation.

* * * * *